(12) United States Patent
Hefetz (10) Patent No.: US 9,295,439 B2
(45) Date of Patent: Mar. 29, 2016

(54) WEIGHT COMPENSATION OF RADIATION DETECTORS

(71) Applicant: General Electric Company, Schenectady, NY (US)

(72) Inventor: Yaron Hefetz, Kibbutz Alonim (IL)

(73) Assignee: General Electric Company, Schenectady, NY (US)

(*) Notice: Subject to any disclaimer, the term of this patent is extended or adjusted under 35 U.S.C. 154(b) by 8 days.

(21) Appl. No.: 14/327,178

(22) Filed: Jul. 9, 2014

(65) Prior Publication Data

US 2016/0007941 A1   Jan. 14, 2016

(51) Int. Cl.
*A61B 6/03* (2006.01)
*A61B 6/00* (2006.01)

(52) U.S. Cl.
CPC ............. *A61B 6/447* (2013.01); *A61B 6/037* (2013.01)

(58) Field of Classification Search
CPC ................................ A61B 6/037; A61B 6/447
See application file for complete search history.

(56) References Cited

U.S. PATENT DOCUMENTS

| | | | |
|---|---|---|---|
| 5,047,641 A * | 9/1991 | Besseling | A61B 6/447 250/363.05 |
| 5,689,543 A | 11/1997 | Graves et al. | |
| 6,279,420 B1 | 8/2001 | Knorowski et al. | |
| 7,280,638 B1 | 10/2007 | Weaver et al. | |
| 7,755,057 B2 | 7/2010 | Kim | |
| 8,479,213 B2 | 7/2013 | Jones et al. | |
| 8,542,892 B2 | 9/2013 | Kovalski | |

* cited by examiner

*Primary Examiner* — Mark R Gaworecki
(74) *Attorney, Agent, or Firm* — Dean D. Small; The Small Patent Law Group, LLC (57) ABSTRACT

An apparatus for capturing images is described herein. The apparatus may include a column attached to a gantry. The column may include a movable section and a radiation detector disposed in the movable section. The apparatus may include a weight compensation unit to apply a force on the movable section opposite to a force of gravity associated with at least the movable section and the radiation detector.

20 Claims, 10 Drawing Sheets

WEIGHT COMPENSATION OF RADIATION DETECTORS

BACKGROUND OF THE INVENTION

The subject matter disclosed herein relates generally to an apparatus and method for diagnostic medical imaging, such as Nuclear Medicine (NM) imaging. In NM imaging, systems with multiple detectors or detector heads may be used to capture an image of a subject, or to scan a region of interest. For example, the detectors may be positioned near the subject to acquire NM data, which is used to generate a three-dimensional (3D) image of the subject.

Some systems may have moving detectors. For example, Single Photon Emission Computed Tomography (SPECT) systems may have moving detector heads, such as gamma detectors positioned to focus on a region of interest. A number of gamma cameras may be moved (e.g., rotated) to different angular positions for acquiring image data. The acquired image data is then used to generate the 3D images.

Resolution of gamma detectors is a convolution of the detector resolution (mainly pixel size) and the collimator resolution. Collimator resolution degrades with the distance of the collimator from the subject. As a result of the configuration of these systems, including the detectors and collimators, the gamma cameras often have to be placed at a distance from the subject, for example to avoid collisions between gamma cameras as the gamma cameras are advanced toward a patient or other object to be imaged. Positioning of the detector heads as the detector heads are radially advanced may result in reduced image quality for detectors that are overly far away from a patient, and/or collisions between detectors as the detectors are positioned, and/or inconvenient lengths of set up time to position the detectors.

The movement of the detector heads may be troublesome due to the weight of the detector heads. In some cases, a detector head may become stuck, preventing a patient from moving, and thereby trapping the patient. In some cases, a broken detector head movement mechanism may result in an unsafe force being applied to the subject.

BRIEF DESCRIPTION OF THE INVENTION

An embodiment relates to an apparatus for capturing images. The apparatus includes a column attached to a gantry. The column includes a movable section and a radiation detector disposed in the movable section. A weight compensation unit applies a force on the movable section opposite to a force of gravity associated with at least the movable section and the radiation detector.

Another embodiment relates to a camera system. The camera system includes a gantry, and a column extending from the gantry. The column includes a movable radiation detector to move towards and away from a potential subject to be positioned towards a center of the gantry. The camera system also includes a counter balanced weight to apply a force on the radiation detector in a direction that is opposite to a gravitational force associated with at least the radiation detector.

Still another embodiment relates to a method of forming a camera system. The method includes attaching a column to a gantry. The attached column has a movable section and a radiation detector disposed in the movable section. The method includes coupling a weight compensation unit to the movable section. The weight compensation unit is configured to apply a force on the movable section opposite to a force of gravity associated with at least the movable section and the radiation detector.

BRIEF DESCRIPTION OF THE DRAWINGS

The present techniques will become more fully understood from the following detailed description, taken in conjunction with the accompanying drawings, wherein like reference numerals refer to like parts, in which.

DETAILED DESCRIPTION OF THE INVENTION

In the following detailed description, reference is made to the accompanying drawings that form a part hereof, and in which is shown by way of illustration of specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the embodiments described herein.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

Various embodiments provide a weight compensation unit implemented in a medical imaging system. In particular, a Nuclear Medicine (NM) imaging system may have a gantry with a plurality of columns and imaging detectors mounted within movable sections of the columns. The imaging system may have a generally radial geometry consisting of an array of the columns uniformly distributed around a bore of the gantry. The movable sections may be independently movable to enhance image quality capability of the imaging system.

Movement of the movable sections may be carried out by a motor. A weight compensation unit is provided including a counter balanced weight to enable ease of movement of the detectors within each movable section.

It should be noted that although the various embodiments are described in connection with a particular NM imaging system, such as a SPECT detector system, the various embodiments may be implemented in connection with other imaging systems, such as a Positron Emission Tomography (PET) imaging system. Additionally, the imaging system may be used to image different objects, including objects other than people.

Figure 1:
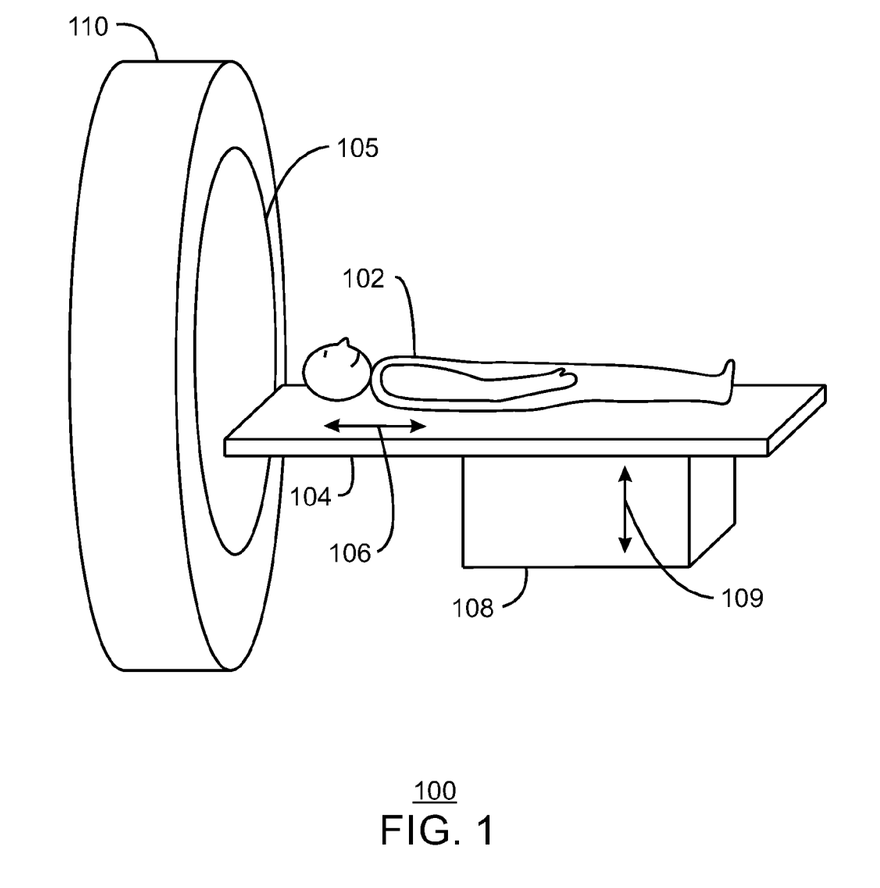
FIG. 1 illustrates a diagram of a medical imaging system.

FIG. 1 illustrates a diagram of a medical imaging system. In the system 100, a subject 102 can be a human patient in one embodiment. It should be noted that the subject 102 does not have to be human. In embodiments, the subject is some other living creature or inanimate object. As illustrated in FIG. 1, the subject 102 can be placed on a pallet 104 that can move a subject horizontally for locating the subject 102 in the most advantageous imaging position within a bore 111 of a gantry 110, as indicated at 106. The bed mechanism 108 can raise and lower the pallet 104 vertically for locating the subject in the most advantageous imaging position, as indicated at 108. A gantry 110 is shown as circular in one embodiment. In other embodiments the gantry 110 may be of any shape such as square, oval, "C" shape, a hexagonal shape, and the like.

Although not illustrated in FIG. 1, the gantry 110 may define an opening wherein the subject 102 may be moved through the opening. As mentioned above, and as discussed in more detail below, columns may extend from the gantry towards the subject 102, and one or more of the columns may be have a weight compensation unit within a movable section to assist movement of the columns.

Figure 2:
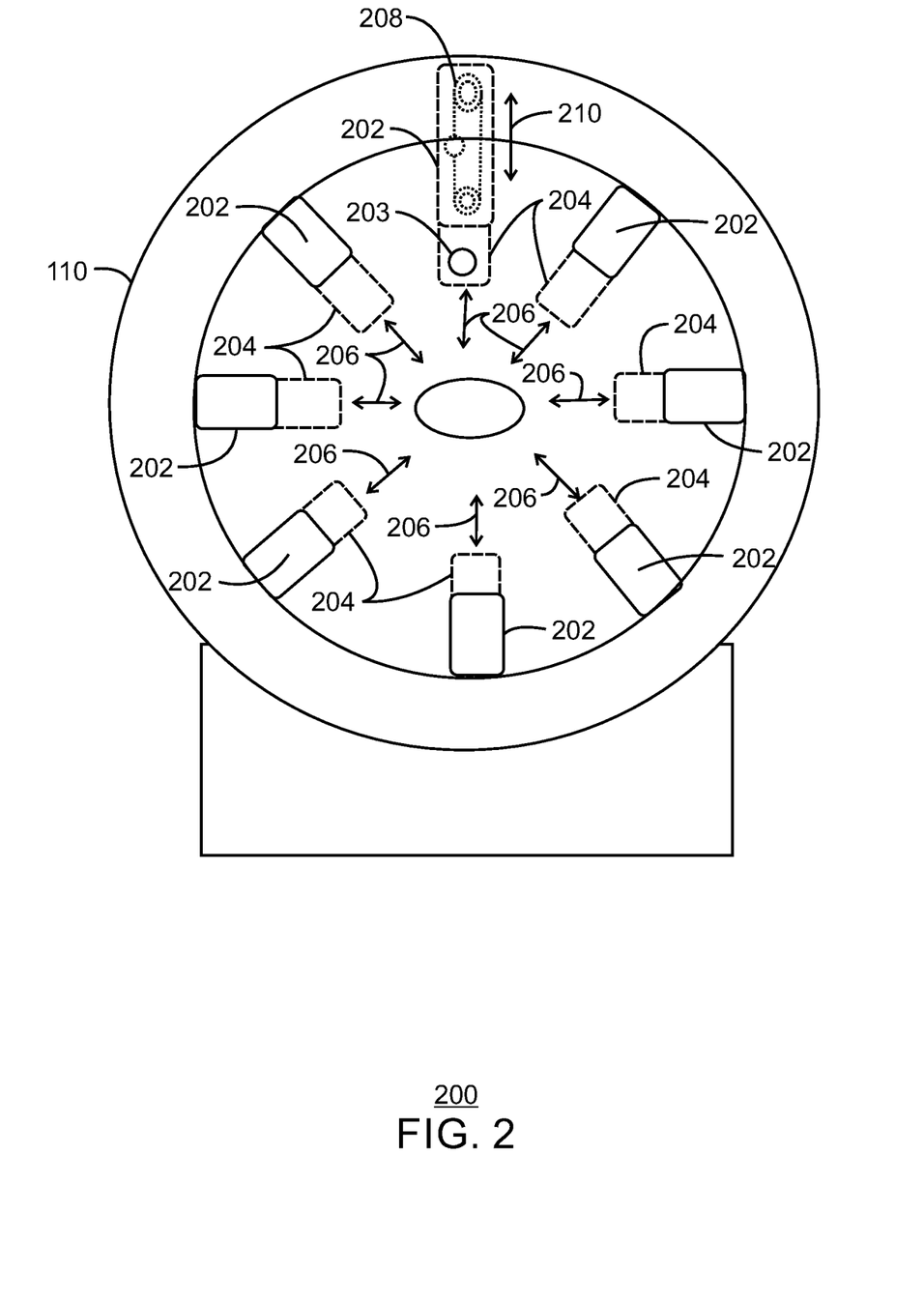
FIG. 2 illustrates a diagram of a front view of a gantry having columns including movable sections.

FIG. 2 illustrates a diagram of a front view of a gantry having columns including movable sections. As illustrated in FIG. 2, the gantry 110 defines an opening that may receive a subject, such as the subject 102 discussed above in regard to FIG. 1. Columns 202 extend from the gantry 110. The columns 202 are configured to house radiation detectors 203 within movable sections 204 of the columns 202. As indicated by the dashed boxes and the arrows 206, the movable sections 206 may be selectively moved toward and away from the subject 102.

As indicated at 208, the movable sections 204 include a weight compensation unit. The weight compensation unit 208 is to provide a counter balance to a weight of the movable sections 204. Although FIG. 2 illustrates only one of the columns 202 having a weight compensation unit 208, a plurality of the columns may include a weight compensation unit, similar to the weight compensation unit 208. In some scenarios, only a portion of the columns 202 may include a weight compensation unit 208. As discussed in more detail below, in some scenarios columns 202 being within 45 degrees from a horizontal axis of the gantry 110 may not include a weight compensation unit since a force of gravity applied to the movable sections 204 within 45 degrees of the horizontal axis is more perpendicular to the direction of movement than columns 202 above 45 degrees.

In embodiments, the column 202 is retractable into the gantry 110. As indicated by the arrow 210, the column 202 may be retracted into the gantry 110, along with the movable section 204. In this embodiment, the weight compensation unit 208 may, at least partially provide a counter balance to the weight both the movable section 204, the column 202, and other components of the column 202.

Figure 3:
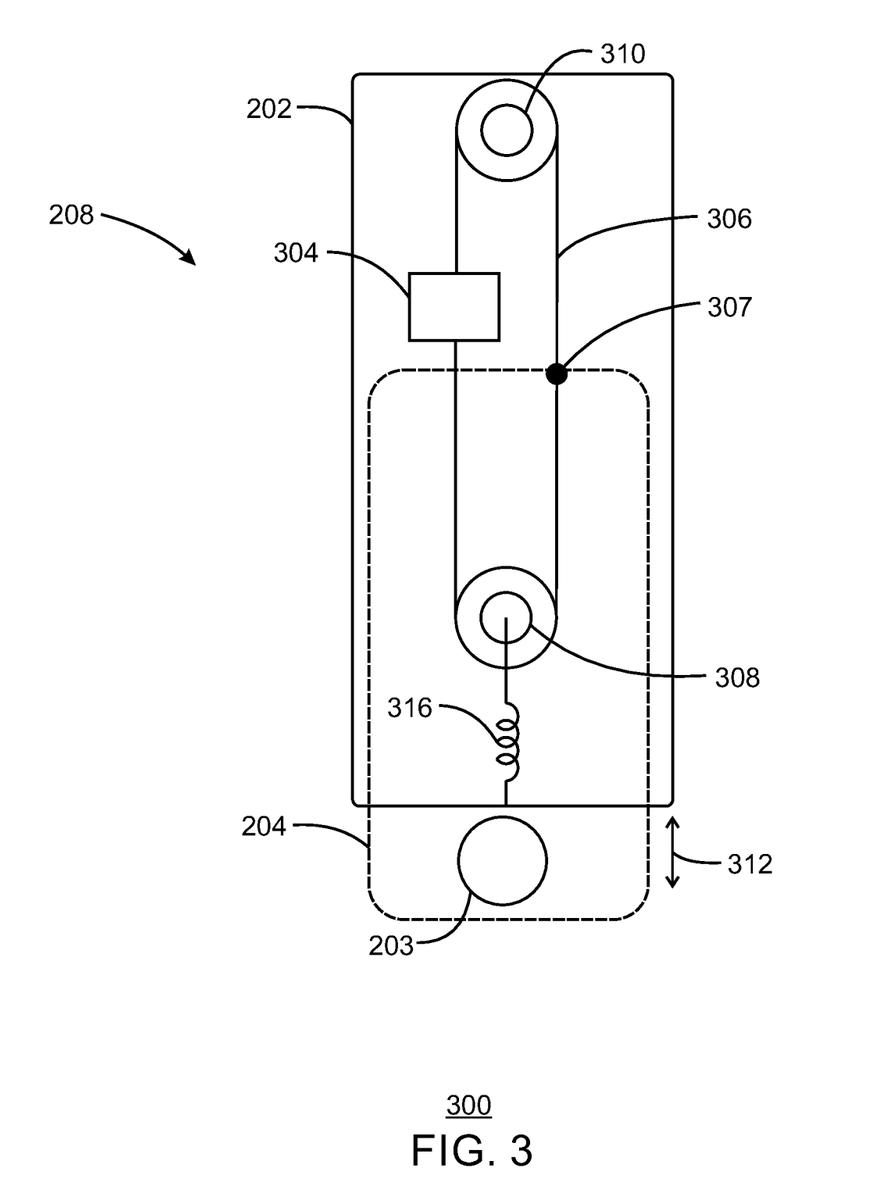
FIG. 3 illustrates a diagram of a side view of one of a column including a weight compensation unit.

FIG. 3 illustrates a diagram of a side view of one of a column including a weight compensation unit. In the example illustrated in FIG. 3, the weight compensation unit, generally indicated by the arrow 208, includes a counter balanced weight 304 coupled to a cable 306. The movable section 204 is attached to the cable 306, as indicated at 307. The movable section 204 is attached to the cable 306 on a side of pulleys 308 and 310 opposite to the counter balanced weight 304, such that when the counter balanced weight 304 moves up, the movable section 204 moves down, and vice versa. In this embodiment, pulleys 308 and 310 are coupled to a stationary section of either the column 202, the gantry 110, or any combination thereof. Motion of the movable section 204 and the counter balanced weight 304 may be restricted and stabilized to moving along a rail (not shown). The pulley 308 may be referred to herein as a lower pulley. The weight compensation unit 208 may also include an upper pulley 310. As indicated by the arrow 312, the movable section 204 may move in and out of the column 202 in order to move a radiation detector 203 closer to, or farther away from, a subject, such as the subject 102 of FIG. 1.

It is important to note that FIG. 3 is an illustrative architecture of one possible arrangement using a counter balanced weight 304 to enable ease of movement of the movable section 204. However, other architectures using a counter balanced weight may be implemented.

Figure 4A:
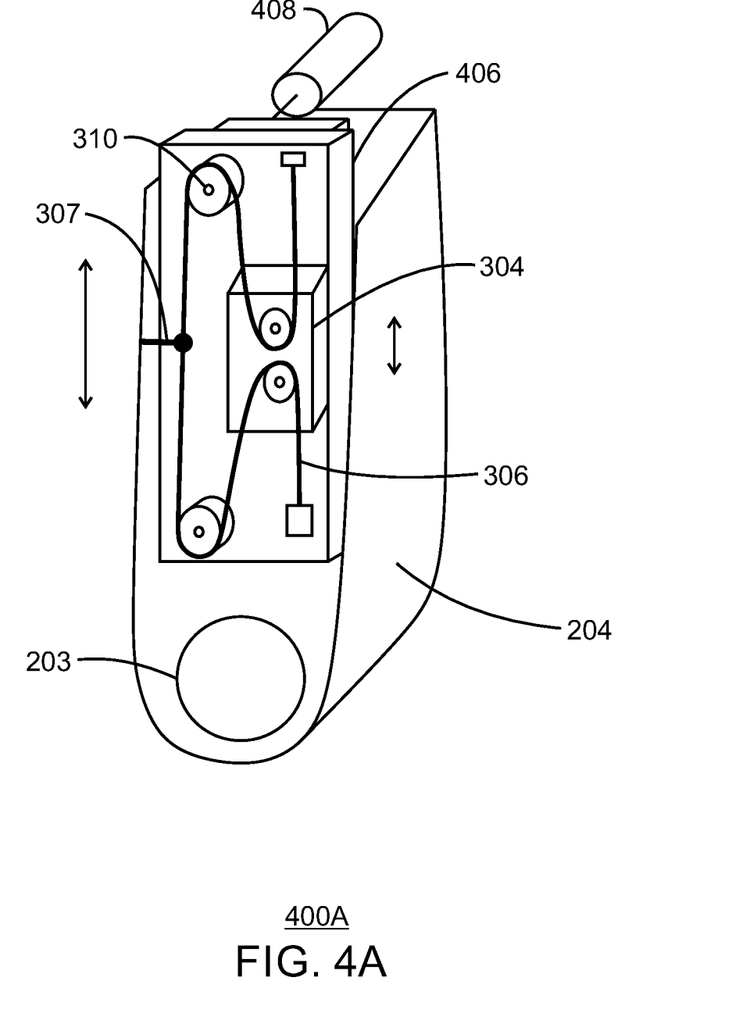
FIG. 4A illustrates a diagram of a perspective view of a column including a weight compensation unit.

FIG. 4A illustrates a diagram of a perspective view of a column including a weight compensation unit. The counter balance weight 304 may be attached to the cable 306. The counter balance weight 304 may route the cable 306 through additional pulleys 402, 404 attached to the counter balanced weight 304. In embodiments, a portion 406 of the weight compensation unit 208 may stationary with respect to the movable section 204. As a motor 408 turns, the upper pulley 310 may engage the belt 306, moving the movable section 204 via an attachment of the movable section 204 to the cable 306, such as the attachment 307 discussed above in regard to FIG. 3.

In some embodiments, the counter balance weight 304 is at least twice as heavy as the radiation detector 203 to enable ease of movement of the movable section 204. In other words, the counter balance weight applies a force opposite to a force of gravity associated with at least the radiation detector 203, and in some embodiments, other various components of the movable section 204.

Figure 4B:
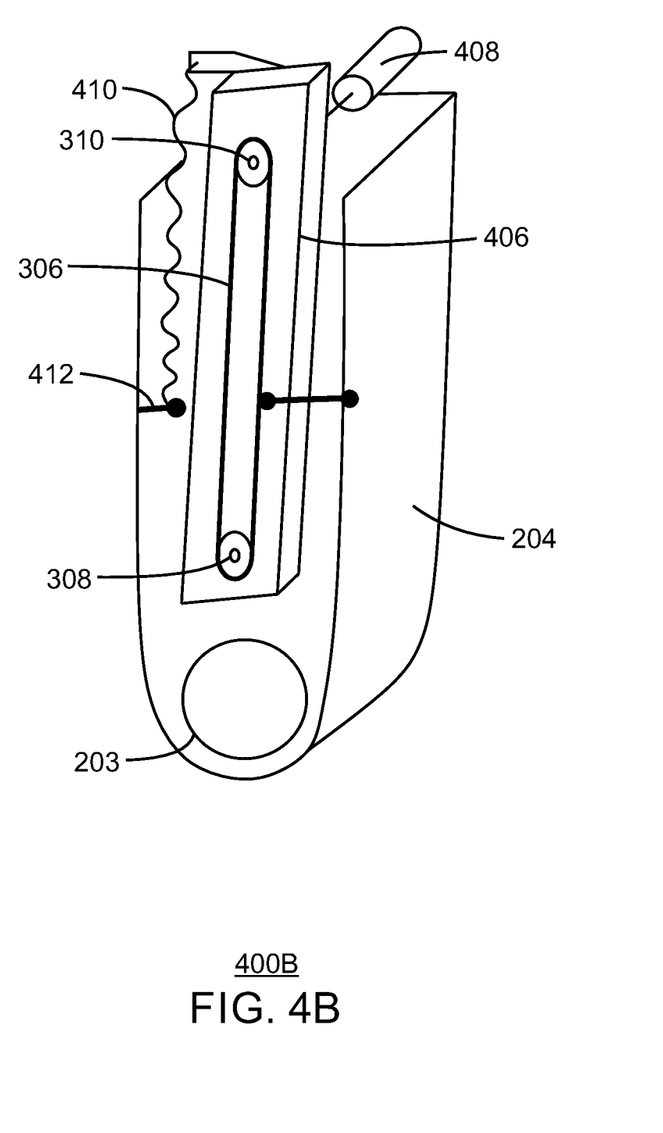
FIG. 4B illustrates a diagram of a perspective view of a column including a weight compensation unit.

FIG. 4B illustrates a diagram of a perspective view of a column including a weight compensation unit. As illustrated in FIG. 4B, the weight compensation unit 208 may also include a spring mechanism 410. The spring mechanism 410 may be connected to the movable section 204, as indicated at 412. The spring mechanism 410 may hold the movable section 204 in tension with the stationary portion 406 of the weight compensation unit.

In embodiments, the spring mechanism 410 is configured to provide tension to the cable 306 between the lower pulley 308 and the upper pulley 310. In operation, as the movable section 204 moves in a direction, the counter balance weight 304 may move in an opposite direction with the spring mechanism 410 providing tightness in the cable 306.

In some embodiments, the column 202 and the movable section 204 may be inverted when the column 202 extends from a lower side of a gantry, such as the gantry 110 discussed above in regard to FIG. 1 and FIG. 2. In this scenario, the weight compensation unit 208 may also be inverted. Therefore, the terms "lower" and "upper" used to describe the pulleys 308 and 310 should not be considered limiting as inverted architectures of the weight compensation unit 208 are contemplated herein.

In some scenarios, the weight compensation unit 208 consisting of the pulleys 308 and 310, and the counter balanced weight 304 may be implemented without the spring mechanism 410. For example, if the column 202 extends from, or near, a bottom of the gantry 110, then the spring mechanism 410 may be compressed, and may not be useful. However, it is contemplated by the techniques described herein that a compression spring mechanism may be used in columns 202 near the bottom of the gantry 110. A compression spring mechanism provides a resistive force when compressed, rather than a force when stretched. In either scenario, the spring mechanism may provide tension on the cable 306 as the movable section 204 is moved in and out of the column 202.

Figure 4C:
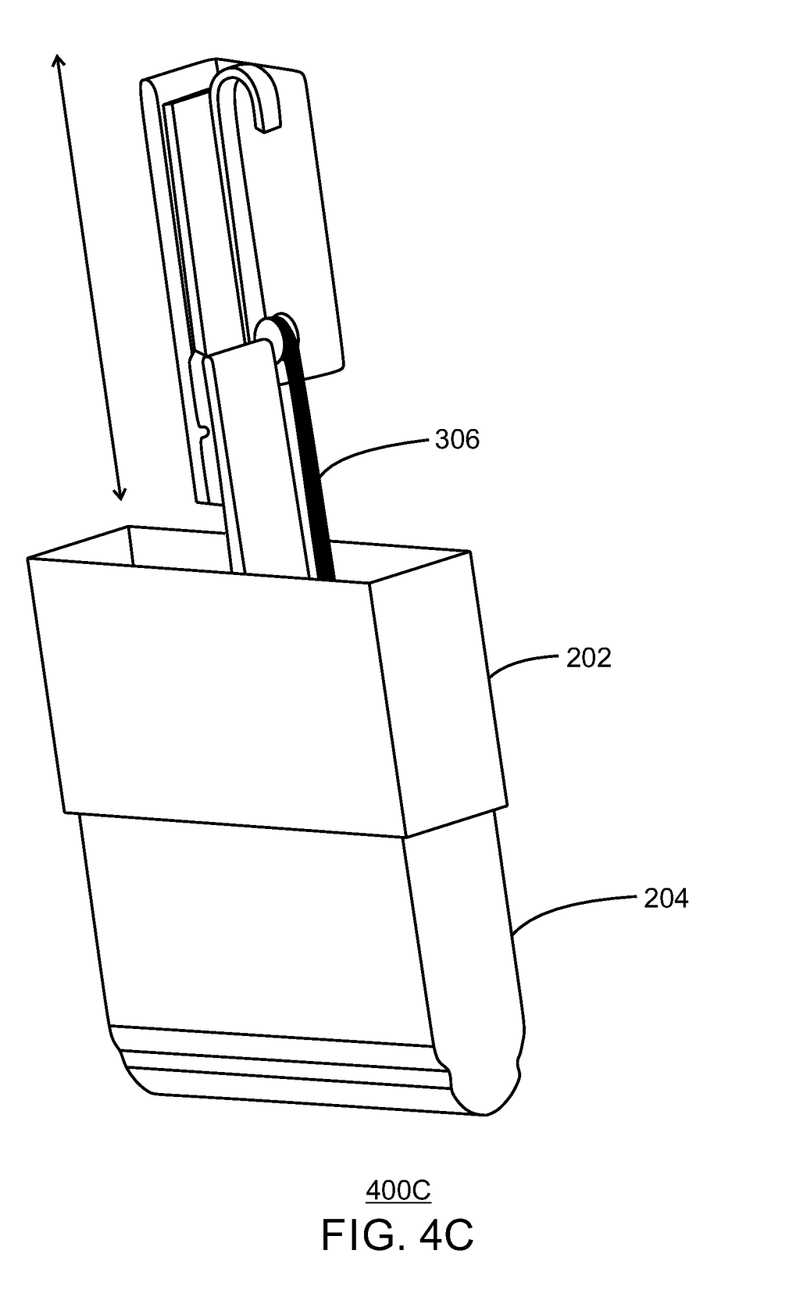
FIG. 4C illustrates a diagram of a perspective view of a column having a movable section attached to a weight compensation unit.

FIG. 4C illustrates a diagram of a perspective view of a column having a movable section attached to a weight compensation unit. As illustrated in FIG. 4C, the movable section 204 may extend outward from the column 202. Although not illustrated in FIG. 4C, the cable 306 is coupled to the movable section 204, and to a weight compensation unit having a counterbalanced weight, such as the counter balanced weight 304.

Figure 5:
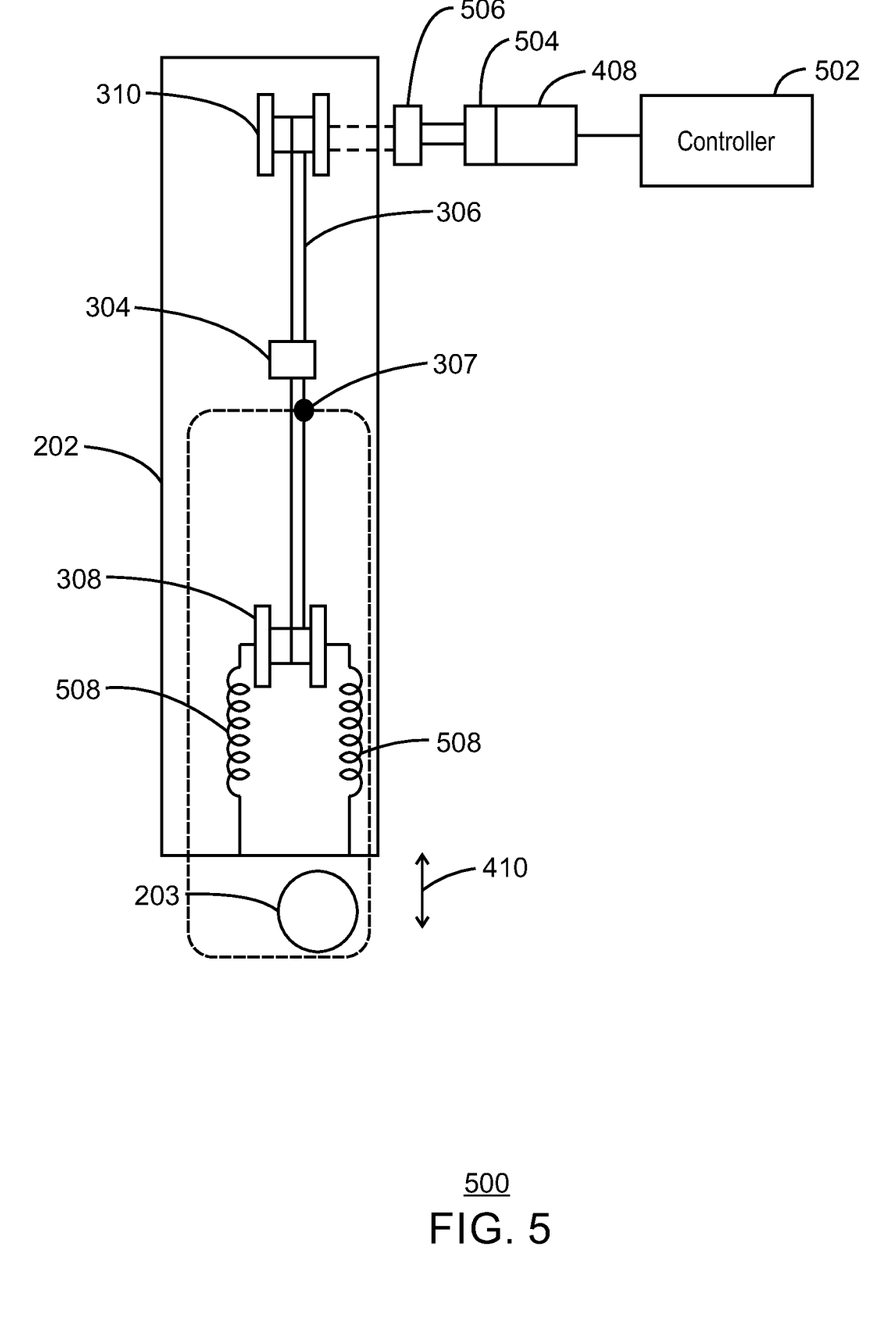
FIG. 5 illustrates a diagram of a front view of the weight compensation unit coupled to a radiation detector.

FIG. 5 illustrates a diagram of the weight compensation unit coupled to a radiation detector. Movement of the radiation detector 203 may be controlled by a controller 502. In embodiments, the controller 506 may be a non-transitory computer-readable medium configured to turn the upper pulley 310. A motor, such as the motor 408 of FIG. 4, may be coupled to a gearbox 504, and a torque limiter 506.

Generally, the controller 502 controls positioning of the movable sections 204 for scanning. The controller 502 may utilize a positioning algorithm or scheme to determine the positions of the various movable sections 204 during scanning, and to position the radiation detectors 203 of the movable sections 204. The radiation detector 203 is configured to collect imaging information. For example, the radiation detector 203 may include a CZT detector configured to collect nuclear medicine imaging information during a scan. Each radiation detector 203 may also include a collimator configured for use with the CZT detector.

As discussed above in reference to FIG. 3, a spring mechanism may be used. In FIG. 5, a spring mechanism 508 may exert tension on the lower pulley 308, and on the cable 306. The motor 408 may be directed by the controller 502 to turn the upper pulley 310 to move the radiation detector 203 in either direction as indicated by the arrow 410. In some embodiments, the controller 502 is a program, or computer-readable instructions, stored on a non-transitory computer-readable medium. The instructions may be carried out by a processing device in order to stop and start the motor, change a direction of motor rotation, and the like, based on user input.

As the motor 402 turns, the upper pulley 310 will also turn based on a gear configuration of the gearbox 504. The gearbox 504 may be configured to automatically switch gears as speed of the motor 402 increases. The rotation of the upper pulley 310 translates to movement of the counter balanced weight 304. Movement of the counter balanced weight 304 may enable movement of the radiation detector 203 with less torque applied to the upper pulley 310 than would otherwise be necessary if the counter balanced weight 304 was not used. For example, the motor 408 may be capable of moving 12 kilograms. However, with the techniques described herein, the motor 408 may only need to move 0.5 kilograms as a result of the counter balanced weight 304 applying a force, via the upper pulley 310, and/or the lower pulley 308, to the radiation detector 203 that is opposite to the force of gravity associated with the radiation detector 203.

In some scenarios, the motor 408 may malfunction. Specifically, the motor 402 may incorrectly push a movable section, such as a movable section 204 of FIG. 2, towards a subject with a dangerous force.

In view of the above, the torque limiter 506 may be used to reduce torque applied to the upper pulley 310, and thus reduce movement of the movable section 204 when the motor 408 malfunctions. In some cases, the torque limiter 506 may be an automatic device that limits the torque applied to the upper pulley 310 by slipping that may occur in a friction plate slip-clutch of the torque limiter 506. For example, torque levels over a predetermined level will cause plates of the torque limiter 506 to slip such that force from the motor 408 may not be applied to the weight compensation unit 208. Other types of torque limiters 506 may be used such as a magnetic particle clutch, a magnetic hysteresis clutch, and the like.

As another example, if the weight of the movable section 204 and the radiation detector 203 is 10 kilograms, and the motor 408 is configured to move up to 12 kilograms, a malfunction in the motor 408 may cause a force of 22 kilograms to be applied to the subject 108. This level of force may be unsafe to the subject 108. Therefore, the torque limiter 506 may limit the amount of torque applied to move the movable section 204 along with the radiation detector 203, such that a malfunction in the motor 408 causing a potentially unsafe condition may be avoided. Specifically, the torque limiter 506 may not engage movement of the upper pulley 310 when a torque associated with an unsafe predetermined force is applied to the torque limiter 506.

Further, in some scenarios, a malfunction in the motor 408 may cause the motor 408 to lock. In this scenario, a subject 102 may be stuck inside the gantry 110, preventing the subject 102 from being removed from the imaging system 100 of FIG. 1. In embodiments, the torque limiter 506 may be asymmetric in that the predetermined limit in terms of torque is higher in a direction towards the subject 108 and less in a direction away from the subject 108. In other words, if the motor 408 is stuck, the force required to cause the torque limiter to slip may be low enough that manual retraction of the movable section 204 may be enabled.

For example, a force of 0.2 kilograms applied to the movable section 204 may allow movement of the movable section 204 towards the subject 102, and a force of 0.8 kilograms applied to the movable section 204 may enable movement of the movable section 204 away from the subject 102.

In some embodiments, the asymmetry of the torque limits may be implemented by a one-way ratchet used in the torque limiter 506 for movement of the movable section 204 away from the subject 108. Other types of release mechanisms are considered. For example, the torque limiter 506 may include a shear pin configured to decouple the motor from the upper pulley 310. Other types of release mechanisms may include a synchronous magnetic torque limiter, wherein magnetic force may be reduced in order to release the motor 408 from the movable section 204, a ball detent torque limiter, a pawl and spring torque limiter, and the like.

Figure 6:
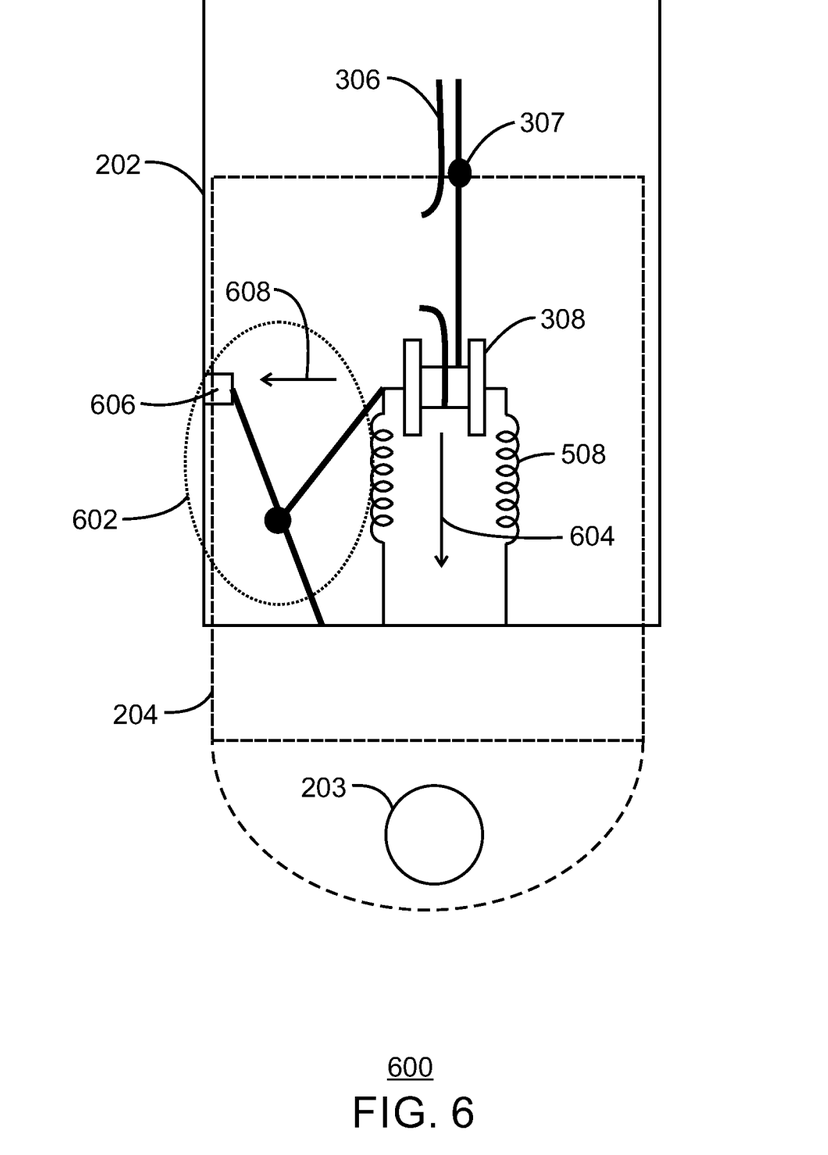
FIG. 6 illustrates a diagram of a front view of a weight compensation unit and a braking mechanism.

FIG. 6 illustrates a diagram of a front view of a weight compensation unit and a braking mechanism. In some scenarios, the cord 306 may break. In this situation, a subject 102 may be dangerously struck by the movable section 204. As illustrated in FIG. 6, a braking mechanism, generally indicated by the dashed circle 602, may be attached to the lower pulley 308. When the cord 306 is broken, the spring mechanism 508 may pull the lower pulley 308 in a direction indicated by the arrow 604. In response, the braking mechanism 602 may force a brake 606 to a side of the column 202, as indicated by the arrow 606, and thereby reducing movement of the movable section 204.

In some embodiments, the movable section 204 may be restricted to movement within a rail disposed within the column 202. In this scenario, the brake 606 may be imposed within the rail such that movement of the movable section 202 is reduced or impinged.

The example illustrated in FIG. 6 is only one example of a braking mechanism. It should be noted that other braking mechanisms and arrangements may be implemented, as known to one having skill in the art. For example, the braking mechanism 602 may be implemented on an upper pulley, such as the upper pulley 310 discussed above in relation to FIG. 3. In any case, a braking mechanism prevents movement of the movable section 204 in the event of cable breakage.

Figure 7:
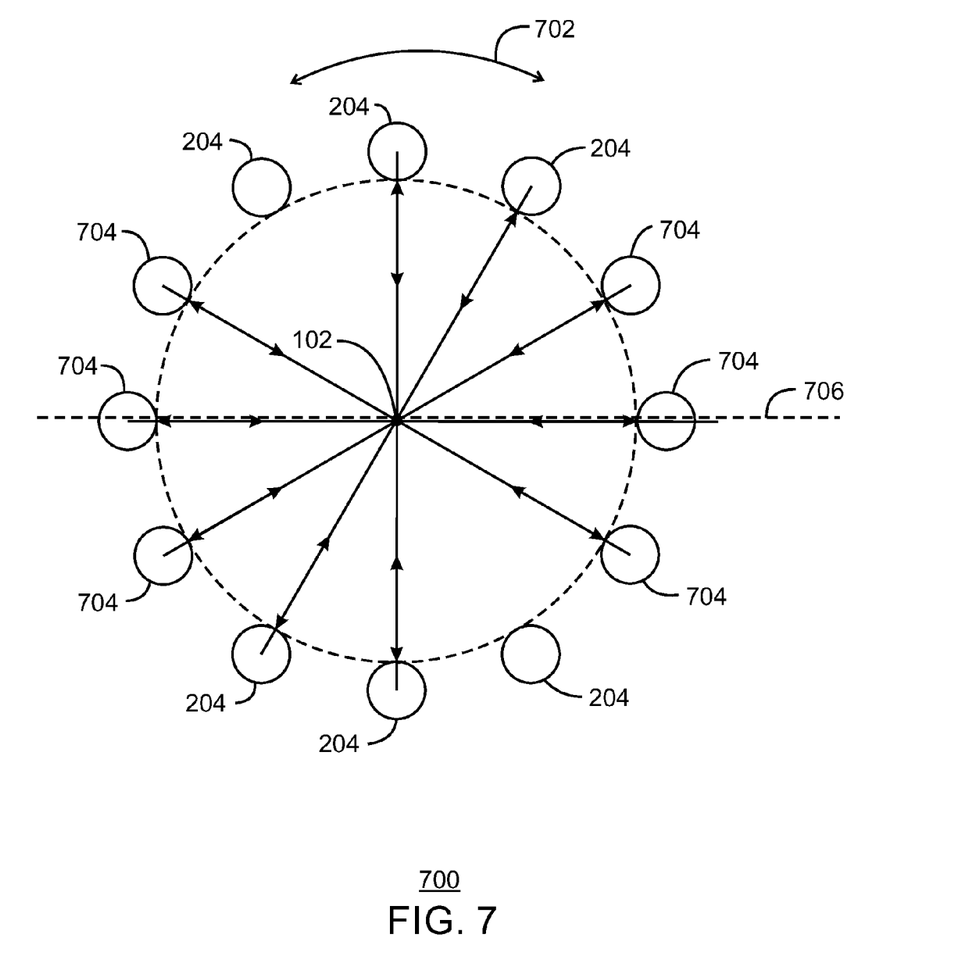
FIG. 7 illustrates a diagram of a front view of a medical imaging system wherein only some of the columns include weight compensation units.

FIG. 7 illustrates a diagram of a front view of a medical imaging system wherein only some of the columns include weight compensation units. As illustrated in FIG. 7, movable sections 204 may move towards and away from the subject 102. In some scenarios, a gantry, such as the gantry 110 of FIG. 1 and FIG. 2, may be configured to rotate, as indicated by the arrow 702. The rotation 702 of the gantry may enable different perspective views to be captured by the imaging system. If the gantry is configured to fully rotate around the subject 102, then each of the movable sections 204 may be connected to a weight compensation unit, such as the weight compensation unit 208, discussed above in reference to FIG. 3.

However, in some scenarios, the gantry may only make minor rotations. In these scenarios, at least some of the movable sections 204 may not be coupled to weight compensations units 208. For example, movable sections 704 closer to a horizontal axis 706 may not be connected to a weight compensation unit 208. As the movable sections 204 are more aligned with the horizontal axis 706, the counter balance weight 304 of the weight compensation unit 208 may be less effective in moving the movable sections 704, when compared to other movable sections 204 that move in a comparatively vertical direction. In embodiments, movable sections 204 that are within 45 degrees of the horizontal axis 706 will not be connected to weight compensation unit 208. This architecture may reduce cost and complexity of the imaging systems described herein, according to one embodiment.

Figure 8:
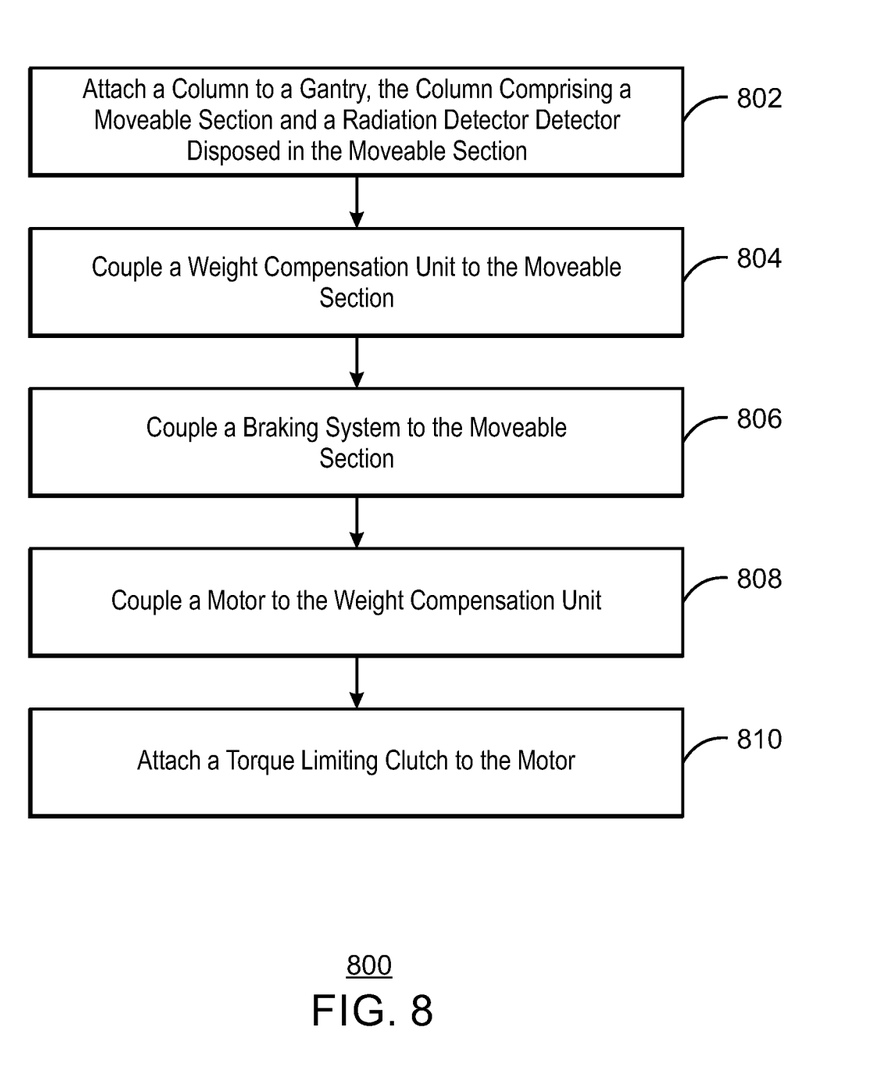
FIG. 8 is a block diagram illustrating a method of forming a camera system.

FIG. 8 is a block diagram illustrating a method of forming a camera system. The method may include attaching a column to a gantry, at block 802. The column is to include a movable section and a radiation detector disposed in the movable section. At block 804, a weight compensation unit is attached to the movable section. The weight compensation unit to apply a force on the movable section opposite to a force of gravity associated with at least the movable section and the radiation detector.

As discussed above in regard to FIG. 3, the weight compensation unit may include a counter balance weight coupled to the movable section with a cable and a lower pulley. An upper pulley may be coupled to a motor configured to move the upper pulley. The movable section may be moved towards and away from a subject, such as a patient placed towards a center of the gantry. In some architectures, the column is one of a plurality of columns. In this scenario, all of the plurality of columns include a radiation detector disposed within a movable section of each column. However, in some embodiments, not all of the movable sections are connected to a weight compensation unit. In some examples, the portion of the movable sections are that are not connected to a weight compensation unit are within 45 degrees from a horizontal axis of the gantry.

In embodiments, the method 800 may include coupling a braking system to the movable section, at block 806. As discussed above in regard to FIG. 6, a braking system may apply pressure or force to a side of a column having the weight compensation unit in the event that a component of the weight compensation unit fails, such as the cable 306 of FIG. 3. The braking system may reduce or prevent injury to a subject, such as a patient, that may otherwise occur.

At block 808, the method 800 may include coupling a motor to the weight compensation unit. At block 810, the method 800 may include attaching a torque limiting clutch to the motor. As discussed above in regard to FIG. 5, the torque limiting clutch may be useful in situations where the motor is stuck, or malfunctions causing increased force to be applied to move the movable section that may cause injury to a subject.

The method 800 may be a method of manufacture or assembly. In some scenarios, the method 800 may be used to modify current systems. In any case, the method 800 may include all or only a portion of the elements discussed in regard to FIG. 8.

While the detailed drawings and specific examples given describe particular embodiments, they serve the purpose of illustration only. The systems and methods shown and described are not limited to the precise details and conditions provided herein. Rather, any number of substitutions, modifications, changes, and/or omissions may be made in the design, operating conditions, and arrangements of the embodiments described herein without departing from the spirit of the present techniques as expressed in the appended claims.

This written description uses examples to disclose the techniques described herein, including the best mode, and also to enable any person skilled in the art to practice the techniques described herein, including making and using any devices or systems and performing any incorporated methods. The patentable scope of the techniques described herein are defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus for capturing images, comprising:
   a column attached to a gantry, the column comprising a movable section and a radiation detector disposed in the movable section; and
   a weight compensation unit positioned within the gantry to apply a force on the movable section opposite to a force of gravity associated with at least the movable section and the radiation detector.

2. The apparatus of claim 1, wherein the weight compensation unit comprises a counter balance weight coupled to the movable section with a cable and pulley, and wherein the movable section is to move towards and away from a potential subject to be positioned towards a center of the gantry.

3. The apparatus of claim 2, wherein the weight of the counter balance weight is at least about twice the combined weight of the movable section and the radiation detector.

4. The apparatus of claim 1, wherein the column is one of a plurality of columns, and wherein all of the plurality of columns comprise a radiation detector disposed within a movable section of each column, and only a portion of the plurality of movable sections of the columns are connected to a weight compensation unit.

5. The apparatus of claim 4, wherein the portion of the plurality of columns without a weight compensation unit are within 45 degrees from a horizontal axis of the gantry.

6. The apparatus of claim 1, further comprising a braking system to reduce movement of the movable section in the event of a disconnection of the counter balanced weight from the movable section.

7. The apparatus of claim 1, further comprising:
a motor to move the movable section; and
a torque limiting clutch to reduce movement of the movable section above a predetermined torque applied by the motor to the torque limiting clutch.

8. The apparatus of claim 1, an emergency release mechanism to release a pulley of the weight compensation unit cable to enable manual movement of the movable section without motor assistance.

9. A camera system, comprising:
a gantry;
a column extending from the gantry, the column comprising a movable radiation detector to move towards and away from a potential subject to be positioned towards a center of the gantry; and
a counter balanced weight to apply a force on the radiation detector in a direction that is opposite to a gravitational force associated with at least the radiation detector, wherein the weight is positioned within the gantry.

10. The system of claim 9, wherein the counter balanced weight is coupled to the radiation detector with a cable and pulley.

11. The system of claim 10, wherein the weight of the counter balanced weight is at least about twice the weight of the radiation detector.

12. The system of claim 9, wherein the column is one of a plurality of columns, and wherein all of the plurality of columns comprise a radiation detector disposed within a movable section of each column, and only a portion of the plurality of movable sections of the columns are connected to a counter balanced weight.

13. The system of claim 12, wherein the portion of the plurality of columns without a counter balanced weight are within 45 degrees from a horizontal axis of the gantry.

14. The system of claim 9, further comprising a braking system to reduce movement of the radiation detector in the event of a disconnection of the counter balanced weight and the radiation detector.

15. The system of claim 9, further comprising:
a motor to move the radiation detector; and
a torque limiting clutch to reduce movement of the radiation detector above a predetermined torque applied by the motor to the torque limiting clutch.

16. The system of claim 9, an emergency release mechanism to release a pulley of the weight compensation unit cable to enable manual movement of the movable section without motor assistance.

17. A method of forming a camera system, comprising:
attaching a column to a gantry, the column comprising a movable section and a radiation detector disposed in the movable section; and
coupling a weight compensation unit to the movable section, the weight compensation unit to apply a force on the movable section opposite to a force of gravity associated with at least the movable section and the radiation detector and positioned within the gantry.

18. The method of claim 17, wherein the weight compensation unit comprises a counter balance weight coupled to the movable section with a cable and pulley, wherein the movable section is to move towards and away from a potential subject to be positioned towards a center of the gantry.

19. The method of claim 17, wherein the column is one of a plurality of columns, and wherein all of the plurality of columns comprise a radiation detector disposed within a movable section of each column, and only a portion of the plurality of movable sections of the columns are connected to a weight compensation unit.

20. The method of claim 17, further comprising:
coupling a braking system to the movable section to reduce movement of the movable section in the event of a disconnection of the counter balanced weight from the movable section;
coupling a motor to the weight compensation unit, wherein the motor is to move the movable section;
attaching a torque limiting clutch to the motor reduce movement of the movable section above a predetermined torque applied to the torque limiting clutch, wherein the torque limiting clutch comprises an emergency release mechanism to release a pulley of the weight compensation unit cable to enable manual movement of the movable section without motor assistance.

* * * * *